United States Patent [19]

Strupczewski et al.

[11] 4,430,335
[45] Feb. 7, 1984

[54] SUBSTITUTED 1-AZASPIRO[4,5]DECANES AND THEIR ANALGESIC COMPOSITIONS

[75] Inventors: Joseph T. Strupczewski, Flemington, N.J.; Beth A. Gardner, San Jose, Calif.

[73] Assignee: Hoechst-Roussel Pharmaceuticals Inc., Somerville, N.J.

[21] Appl. No.: 465,146

[22] Filed: Feb. 9, 1983

[51] Int. Cl.³ ............... C07D 221/20; A61K 31/445
[52] U.S. Cl. .................................. 424/267; 424/274; 548/408; 546/16
[58] Field of Search .................. 548/408; 546/16; 424/274, 267

[56] References Cited

PUBLICATIONS

Schipper et al., "J. Organic Chemistry", vol. 26, pp. 4135–4137 (1961).
Rice "J. Medicinal Chemistry", vol. 8, pp. 825–830 (1965).

Primary Examiner—Robert T. Bond
Attorney, Agent, or Firm—Jerome Rosenstock

[57] ABSTRACT

This invention relates to substituted 1-azaspiro[4.5] decanes and 1-azaspiro[5.5]undecanes of the formula

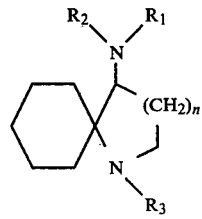

wherein $R_1$ is hydrogen, $-CO_2R_4$, $R_4$; $R_2$ is hydrogen,

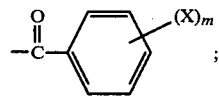

$R_3$ is hydrogen,

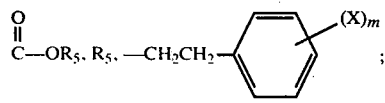

$R_4$ is alkyl of 1 to 4 carbon atoms; $R_5$ is alkyl of 1 to 8 carbon atoms; X is halogen, alkyl of 1 to 4 carbon atoms, alkoxy of 1 to 4 carbon atoms, $CF_3$, and OH; m is an integer of 0, 1 or 2; and n is an integer of 1 or 2.

52 Claims, No Drawings

SUBSTITUTED 1-AZASPIRO[4,5]DECANES AND THEIR ANALGESIC COMPOSITIONS

To the best of our knowledge the compounds of the present invention have not heretofore been described or suggested.

The compounds of the present invention have the general formula

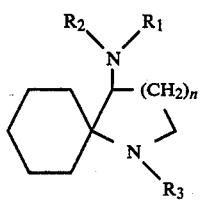

wherein $R_1$ is hydrogen, $-CO_2R_4$, $R_4$; $R_2$ is hydrogen,

$R_3$ is hydrogen,

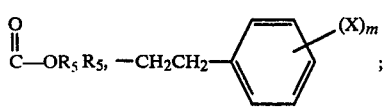

$R_4$ is alkyl of 1 to 4 carbon atoms; $R_5$ is alkyl of 1 to 8 carbon atoms; X is halogen, alkyl of 1 to 4 carbon atoms, alkoxy of 1 to 4 carbon atoms, $CF_3$, and OH; m is an integer of 0, 1 or 2; and n is an integer of 1 or 2.

In the above definitions the term "alkyl" refers to a straight or branched chain hydrocarbon containing no unsaturation, e.g. methyl, ethyl, isopropyl, 2-butyl, neopentyl, n-hexyl, etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; and the term "halogen" refers to a member of the family consisting of fluorine, chlorine, bromine and iodine.

Preferred compounds of the invention are those where $R_1$ is

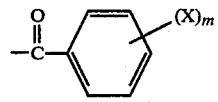

and $R_3$ is $R_5$.

The compounds of the present invention are prepared in the following manner. The substituents $R_1$ to $R_5$, X, and the integers m and n are as defined above unless indicated otherwise.

Utilizing the procedure described by J. R. Piper, C. R. Stringfellow, Jr. and T. P. Johnston, *J. Med. Chem.* 9, 911 (1966), a 1-aminocyclohexane carboxylate, e.g. an ethylcarboxylate, is prepared having the formula (II)

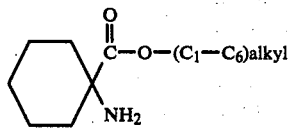

Compound II is reacted with halo ester having the formula

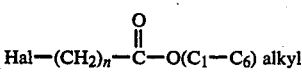

where Hal is a halogen, under conventional substitution reaction conditions, typically in the absence of a solvent, and in the presence of a base as an acid scavenger, a temperature of 100° to 120° C. for 72 to 120 hours to form compound IV having the formula

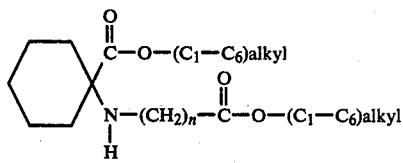

Alternatively, Compound II is reacted with Compound (V) of the formula

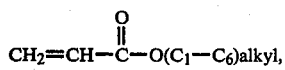

in a protic solvent, e.g. ethanol, propanol, at a temperature of 78° to 100° C., for 16 to 24 hours to form Compound IV.

Compound IV is then subjected to a condensation or cyclization reaction whereby Compound (IV) is cyclized to form Compound VI.

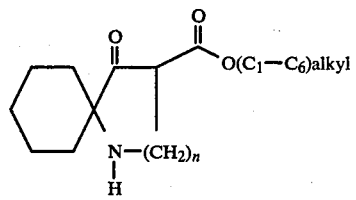

Typically, this cyclization is carried out in a hydrocarbon solvent, e.g. benzene, toluene, xylene in the presence of a strong base, e.g. NaH, KH, $NaOC_2H_5$, at a temperature of 80° to 140° C. for 4 to 24 hours.

Compound (VI) is then subjected to hydrolysis of the ester and subsequent decarboxylation to yield Compound (VII)

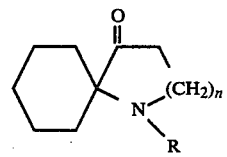

Such hydrolysis and decarboxylations are typically carried out in refluxing dilute aqueous mineral acids at a temperature of 90° to 120° C. for 4 to 16 hours.

In an alternative procedure, Compound IV is reacted with a halide having the formula Hal-R₃ where Hal is a halogen, and R₃ is other than hydrogen, under conventional substitution reaction conditions, typically in the presence of a halocarbon solvent e.g. CHCl₃, 1,2-dichloroethane, at a temperature of 60° to 85° C. for 16 to 24 hours to form compound VIII

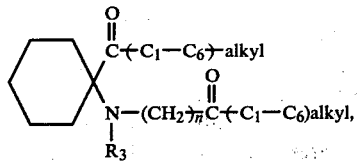

where R₃ is other than hydrogen. Compound VIII in turn is cyclized and decarboxylated as described above, to form compound IX

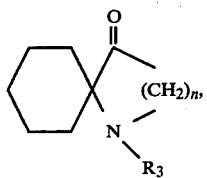

where R₃ is other than hydrogen.

Compounds VII or IX can be reacted in a conventional fashion, e.g. via reductive alkylation, with an amine R₁NH₂ to form a compound of the invention

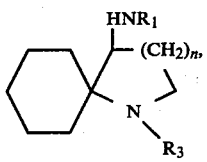

where R₁ is other than hydrogen, a reducing agent such as hydrogen with platinum or Raney nickel, sodium, sodium amalgam, metal hydrides in alcohol, dimethylamine borane etc., is employed to obtain compound X, where R₁ is other than hydrogen.

In a preferred method, compound VII or IX is reacted with a secondary amine, R₁NH₂, preferably methylamine, in the presence of a Lewis acid, preferably titanium tetrachloride, in a hydrocarbon solvent, e.g. benzene, toluene, etc. in an inert atmosphere at 80° to 110° for 3 to 16 hours to form an imine

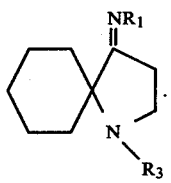

The subsequent intermediate imine XI is reduced by a metal hydride, sodium borohydride being preferred, in a protic solvent e.g. ethanol, isopropanol etc., at 25° to 82° C. for 18 to 24 hours to form Compound (I), where R₁ is alkyl.

Alternatively, Compound (I) of the invention can be obtained by reaction of compounds VII or IX via the conventional Leuckart-Wallach reaction with an amine having the formula

In a preferred method, Compound VII or IX is reacted with sodium cyanoborohydride (NaBH₃CN) and ammonium acetate in a protic solvent, e.g. methanol, isopropanol, etc. at a temperature of 64° to 82° C. for 16 to 48 hours to form Compound XI (Compound I where R₁ and R₂ are hydrogen)

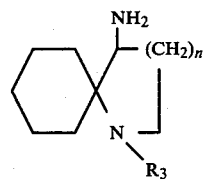

Compound X is typically reacted with a halide of the formula

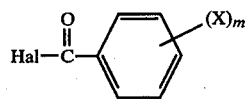

where Hal is a halogen, to form a compound of the invention

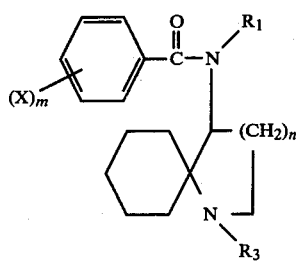

This displacement reaction is conventional and is carried out in a halocarbon solvent, e.g., CHCl₃, 1,2-dichloroethane, etc. at a temperature of 60° to 85° C. for 3 to 24 hours. It is also carried out under conventional Schotten-Baumann reaction conditions.

Compound XI is typically reacted in a conventional manner under displacement reaction conditions whereby it is reacted with (1) Hal-R₁ where Hal is a halogen and R₁ is other than hydrogen or (2) Hal-R₂ where Hal is a halogen and R₂ is other than hydrogen to form a compound (XIV) of the invention

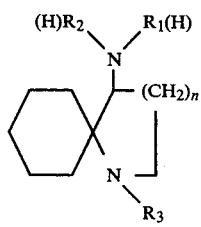

(XIV)

Where $R_1$ or $R_2$ is hydrogen, the resultant Compound XIV can be further reacted with Hal-$R_1$ or Hal-$R_2$, respectively, to form compound XV of the invention where $R_1$ and $R_2$ are other than hydrogen

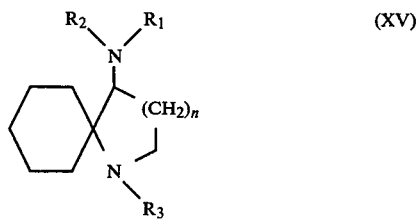

(XV)

where $R_1$ and $R_2$ are not hydrogen.

The compounds (I) of the present invention are useful as analgesics. The procedure employed here for evaluating the analgesic activities of the compounds I is a modification of Siegmund et al. Proc. Soc. Exptl. Biol. Med., 95 729 (1957). Thus, 12.5 mg of phenylquinone (phenyl-p-benzoquinone) is dissolved in 5 ml of 95% ethanol and diluted to 100 ml with distilled water and administered to mice (10 ml/kg, intraperitoneally [i.p.]). This produces a characteristic "writhe" which is defined as an inward rotation of one or more feet with twisting and turning of the trunk, drawing in of the abdominal wall, lordosis and arching of the back.

A total of 28 male, CD-1 mice (18 to 30 grams) are employed for a time response. Animals receive food and water ad libitum. Drugs to be tested are prepared with distilled water, and if insoluble, one drop of a suitable surfactant is added.

Twenty animals (5/group) are administered the drug subcutaneously (sc) 15, 30, 45 and 60 minutes prior to phenylquinone injection. Control animals (2/group) receive an equal amount of vehicle. After the administration of phenylquinone, the mice are placed separately into one-liter beakers and 5 minutes are allowed to elapse. The mice are then observed for a period of 10 minutes and the number of writhes are recorded for each animal. The formula for computing percent inhibition is:

$$\frac{x \text{ Writhes in Control Group} - x \text{ Writhes in Drug Group}}{x \text{ Writhes in Control Group}} \times 100$$

The time period with the greatest percent of inhibition is considered the peak time.

A dose range is run in the same fashion as a time response except ten animals per group are tested at the peak time of drug activity. Fifty animals, four drug groups, and a vehicle control are employed. Animals are dosed and tested in a randomized manner. An estimated $ED_{50}$ is calculated by a computer linear regression analysis.

The analgesic activities of various compounds of the invention are presented in Table I. The data presented therein were determined in accordance with the above described procedures.

TABLE I

| Analgesic Activities (as measured in the phenylquinone writhing test) | | |
|---|---|---|
| Compound | % Inhibition | Dose Subcutaneously (sc) [*= $ED_{50}$] |
| 1-ethoxycarbonyl-4-amino-1-azaspiro[4.5]decane hydrochloride | 50 | 13.1* |
| 1-methyl-4-(3,4-dichlorobenzamido)-1-azaspiro[4.5]decane hydrochloride | 50 | 1.1* |
| 1-methyl-4-(2,4-dichlorobenzamido)-1-azaspiro[4.5]decane hydrochloride | 50 | 23.9* |
| 1-methyl-4-(3-chlorobenzamido-1-azaspiro[4.5]decane | 50 | 7.0* |
| 1-methyl-4-(4-fluorobenzamido)-1-azaspiro[4.5]decane fumarate | 50 | 0.5* |
| 1-methyl-4-benzamido-1-azaspiro[4.5]decane fumarate | 50 | 6.8* |
| 1-methyl-4-(4-methylbenzamido)-1-azaspiro[4.5]decane fumarate | 50 | 2.2* |
| 1-methyl-4-(p-methoxybenzamido)-1-azaspiro[4.5]decane hemifumarate | 50 | 1.1* |
| 1-methyl-4-(N—methyl-3,4-dichlorobenzamido)-1-azaspiro[4.5]decane | 50 | 3.5* |
| 1-ethoxycarbonyl-4-(2,4-dichlorobenzamido)-1-azaspiro[4.5]decane | 48% | 25 |
| 1-ethoxycarbonyl-4-(3,4-dichlorobenzamido)-1-azaspiro[4.5]decane | 49% | 25 |
| 1-ethoxycarbonyl-4-(N—methylbenzamido)-1-azaspiro[4.5]decane | 45% | 25 |
| 1-ethoxycarbonyl-4-amino-1-azaspiro[4.5]decane hydrochloride | 50 | 13.1* |
| morphine sulfate | 50 | 0.52* |
| propoxyphine | 50 | 3.4* |
| 1-ethoxycarbonyl-5-(3,4-dichlorobenzamido)-1-azaspiro[5.5]undecane | 50 | 13.1* |

The above compounds of the invention compare favorably with the standard analgesics morphine sulfate and propoxyphine which are also listed above and tested as described.

Effective quantities of the compounds of the invention may be administered to a patient by any one of various methods, for example, orally as in capsules or tablets, parenterally in the form of sterile solutions or suspensions, and in some cases intraveneously in the form of sterile solutions. The free base final products, while effective themselves, may be formulated and administered in the form of their pharmaceutically acceptable addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. The preparation should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains 1.0 to 100 milligrams of active compound.

The tablets, pills, capsules, troches, and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin; and a flavoring agent such as peppermint, methyl salicylate, or orange flavoring. When the dosage unit is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac or other enteric coating agents. A syrup may contain, in addition to the active compounds, sucrose, as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain a pharmaceutically effective amount, i.e., at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or suitable dose vials made of glass or plastic.

The invention is illustrated by the following examples wherein unless indicated otherwise, the temperature indicated is in degrees Centigrade.

EXAMPLE 1

(a) Ethyl-1-aminocyclohexanecarboxylate

Following the procedure of J. R. Piper et al, *J. Med. Chem.*, 9, 911 (1966), to 100 g of NaCN (2.0 mole) in 200 ml of water was added 118 g $NH_4Cl$ (212 mole) in 300 ml of water and 135 ml. of $NH_4OH$ (2.0 mole). The resultant mixture was cooled in an ice-water bath and to it was added 198.4 g. cyclohexanone (2.0 mole) in 350 ml of methanol. The resultant mixture was stirred overnight (about 18 hours), cooled and then slowly poured into 1600 ml of concentrated HCl (Sp. g. 1.18) cooled to 0° C. The reaction mixture was saturated with HCl gas and then allowed to stand overnight. 800 ml of concentrated HCl was again added and the reaction mixture was again saturated with HCl gas. The resultant mixture was refluxed for 7 hours and stirred overnight (about 16 hours) at room temperature. The mixture was evaporated to yield a solid to which was added 1 L of ethanol saturated with HCl gas. The resultant mixture was refluxed for 7 hours and then 2 ml of benzene was added. The mixture was distilled to a residue which was dissolved in 2 L of ether and 300 ml of absolute ethanol and then cooled in an ice bath. The solution was then saturated with $NH_3$ gas and the resultant solid was filtered. The filtrate was concentrated and then distilled at 77° C. to yield 115 g of ethyl-1-aminocyclohexanecarboxylate.

(b) Ethyl 1-(ethoxycarbonylethylamino)cyclohexanecarboxylate hydrochloride

A stirring mixture of ethyl 1-aminocyclohexanecarboxylate (46.7 g, 0.27 mole) of Example 1a, powdered $K_2CO_3$ (37.5 g, 0.27 mole) and ethyl 3-bromopropionate (49.2 g, 0.27 mole) was heated between 100°–105° C. for 3 days. After cooling to ambient temperature the mixture was poured into $H_2O$ and the aqueous mixture extracted with ether. The ether extracts were dried ($Na_2SO_4$) and the solvent removed under reduced pressure to give 63.1 g of a liquid. The liquid was fractionally distilled, and the desired product distilled at 108°–110° C., 0.35 mm to yield 31.5 g (43%) of a liquid. A hydrochloride salt was prepared by bubbling HCl into an ethereal solution of the free base (2.5 g), and collecting the resultant insoluble hydrochloride salt. The resultant salt was recrystallized from ethyl acetate-hexane (twice) to yield 1.7 g of the ethyl 1-(ethoxycarbonylethylamino)cyclohexanecarboxylate hydrochloride, m.p. 148°–150° C.

ANALYSIS: Calculated for $C_{14}H_{25}NO_4 \cdot HCl$: 54.62%C; 8.51%H; 4.55%N. Found: 54.60%C; 8.61%H; 4.54%N.

(c) Ethyl 1-(N-ethoxycarbonyl-2-ethoxycarbonylethylamino) cyclohexane carboxylate To a stirred mixture of ethyl-1(ethoxycarbonylethylamino) cyclohexane carboxylate of Example 1b (10.0 g. 0.037 mole), $NaHCO_3$ (3.7 g, 0.044 mole) and $CHCl_3$ (100 ml) was added, dropwise, ethyl chloroformate (4.8 g, 0.044 mole) in $CHCl_3$ (20 ml). The mixture was stirred and refluxed for 16 hours, poured into $H_2O$ and the organic layer separated. The organic phase was washed with 3 N HCl, water, and dried ($Na_2SO_4$). Removal of the solvent under reduced pressure gave 13.3 g of a liquid which distilled at 159°–162° C., 0.4 mm to give ethyl 1-(N-ethoxycarbonyl-2-ethoxycarbonylethylamino)cyclohexane carboxylate as a liquid, 10.4 g (69%).

ANALYSIS: Calculated for $C_{14}H_{29}NO_6$: 59.45%C; 8.51%H; 4.08%N. Found: 59.62%C; 8.58%H; 3.98%N.

(d) 1-Ethoxycarbonyl-1-azaspiro[4.5]decane-4-one

To a stirring suspension of NaH (99%, 1.8 g, 0.075 mole) in dry benzene (60 ml) under nitrogen was added, dropwise, ethyl 1-(N-ethoxycarbonyl-2-ethoxycarbonylethylamino) cyclohexane carboxylate (11.9 g, 0.035 mole) in benzene (25 ml). The mixture was stirred and refluxed for 4 hours, poured into 3 N HCl, ether added and the layers separated. The aqueous phase was extracted with ether, the excess combined, washed with H₂O, dried (Na₂SO₄) and the solvent removed under reduced pressure to give a liquid. The liquid was refluxed in 6 N HCl for 4 hours, the cooled mixture extracted with ether, the ether extract washed with saturated NaHCO₃, water, dried (Na₂SO₄) and the solvent removed under reduced pressure to give 5.0 g of an oil, which solidified when scratched with a glass rod. The solid was recrystallized from ethanol-water and then twice from petroleum ether (30°–60° C.), at −77° C. to give 2.0 g (25%) of a solid of 1-ethoxycarbonyl-1-azaspiro[4.5]decane-4-one, m.p. 72°–74° C.

ANALYSIS: Calculated for $C_{12}H_{19}NO_3$: 63.97%C; 8.50%H; 6.22%N. Found: 63.94%C; 8.62%H; 6.12%N.

(e) 1-Ethoxycarbonyl-4-amino-1-azaspiro[4.5]decane hydrochloride

A solution of 10.0 g (0.045 mole) of 1-ethoxycarbonyl-1-azaspiro[4.5]decane-4-one of Example 1d, 33.6 g (0.45 mole) of ammonium acetate, 2.0 g (0.031 mole) of NaBH₃CN and 150 ml of dry methanol was stirred and refluxed over 3 A molecular sieves for 18 hours. The reaction was cooled, acidified with concentrated HCl to pH 2, then the solvent was removed under reduced pressure. The residue was dissolved in 150 ml of H₂O and extracted once with ether. The aqueous solution was then basified with solid KOH to a pH 10, saturated with NaCl, and extracted with ether. The ether extracts were dried over Na₂SO₄ and the solvent removed under reduced pressure to give 7.3 g (73%) of an oil. The hydrochloride salt was made by dissolving 2.0 g of oil in ether and bubbling in HCl gas. The solid was collected and recrystallized twice from ethanol-ether to give 1.5 g of 1-ethoxycarbonyl-4-amino-1-azaspiro[4.5]decane hydrochloride, m.p. 235°–236° C.

ANALYSIS: Calculated for $C_{12}H_{22}N_2O_2 \cdot HCl$: 54.85%C; 8.82%H; 10.66%N; 13.49%Cl. Found: 54.92%C; 8.90%H; 10.91%N; 13.69%Cl.

EXAMPLE 2

1-Methyl-4-amino-1-azaspiro[4.5]decane difumarate

To a refluxing suspension of 1.7 g (0.046 mole) of lithium aluminum hydride (LAH) in 50 ml of tetrahydrofuran (THF) was added dropwise a solution of 5.1 g (0.23 mole) of 1-ethoxycarbonyl-4-amino-1-azaspiro[4.5]decane of Example 1e in 50 ml of tetrahydrofuran (THF). The reaction was refluxed for 3 hours under nitrogen, stirred overnight (about 16 hours) at room temperature, cooled in an ice bath and water was added until there was no hydrogen evolution. The reaction was filtered and the filtrate was extracted with 3 N HCl solution. The acidic extracts were basified, then extracted with ether, washed with saturated NaCl solution and dried over Na₂SO₄. The solvent was removed to give 2.6 g of oil which was distilled at 55°–58° C., and 0.15 mm. The fumarate salt was made by adding a solution of 1.7 g of 1-methyl-4-amino-1-azaspiro[4.5]decane in 10 ml of isopropanol to a hot saturated solution of fumaric acid in isopropanol. The precipitate was recrystallized once from ethanol to give 1.5 g (11%), m.p. 165°–167° C. of 1-methyl-4-amino-1-azaspiro[4.5]decane difumarate.

ANALYSIS: Calculated for $C_{18}H_{28}N_2O_8$: 53.99%C; 7.05%H; 7.00%N. Found: 53.94%C; 7.05%H; 7.34%N.

EXAMPLE 3

1-Methyl-4-(3,4-dichlorobenzamido)-1-azaspiro[4.5]-decane hydrochloride

To a stirring suspension of 3.0 g (0.017 mole) of 1-methyl-4-amino-1-azaspiro[4.5]decane of Example 2 and 5.0 g of NaHCO₃ in 50 ml of CHCl₃ was added dropwise 3.8 g (0.018 mole) of 3,4-dichlorobenzoyl chloride in 25 ml of CHCl₃. The reaction was refluxed for 3 hours, cooled to room temperature, filtered, and the solvent evaporated to give an oil. The residue was triturated with boiling hexane and decanted, the hexane solution afforded 2.6 g of 1-methyl-4-(3,4-dichlorobenzamido)-1-azaspiro[4.5]decane on standing. The solid was dissolved in ether and a solution of ethereal HCl was added. The resulting solid was collected and recrystallized three times from ethanol to give 2.2 g (35%) m.p. 227°–228° C. of 1-methyl-4-(3,4-dichlorobenzamido)-1-azaspiro[4.5]decane hydrochloride.

ANALYSIS: Calculated for $C_{17}H_{22}Cl_2N_2O \cdot HCl$: 54.05%C; 6.14%H; 7.42%N; 28.16%Cl. Found: 54.32%C; 6.11%H; 7.21%N; 28.16%Cl.

EXAMPLE 4

1-Methyl-4-(2,4-dichlorobenzamido)-1-azaspiro[4.5]-decane hydrochloride

To a stirring suspension of 3.0 g (0.017 mole) of 1-methyl-4-amino-azaspiro[4.5]decane of Example 2 and 5.0 g of NaHCO₃ in 50 ml of CHCl₃ was added dropwise 3.8 g (0.018 mole) of 2,4-dichlorobenzoyl chloride in 25 ml of CHCl₃. The reaction was refluxed for 3 hours, cooled to room temperature, filtered, and the solvent evaporated to give an oil. The residue was triturated with boiling hexane and decanted; the hexane solution afforded 3.1 g of 1-methyl-4-(3,4-dichlorobenzamido)-1-azaspiro[4.5]decane on standing. The solid was dissolved in ether and a solution of ethereal HCl was added. The resulting solid was collected and recrystallized three times from ethanol to give 2.4 g (37.5%) m.p. 227°–229° C. of 1-methyl-4-(2,4-dichlorobenzamido)-1-azaspiro[4.5]decane hydrochloride.

ANALYSIS: Calculated for $C_{17}H_{22}Cl_2N_2O \cdot HCl$: 54.05%C; 6.14%H; 7.42%N; 28.16% Cl. Found: 54.14% C; 6.10%H; 7.45%N; 28.07%Cl.

EXAMPLE 5

1-Methyl-4-(3-chlorobenzamido)-1-azaspiro[4.5]decane

To a stirring suspension of 3.8 g (0.023 mole) of 1-methyl-4-amino-1-azaspiro[4.5]decane of Example 2 and 6.0 g of NaHCO₃ in 50 ml of CHCl₃ was added dropwise 4.6 g (0.026 mole) of m-chlorobenzoyl chloride in 25 ml of CHCl₃. The reaction was refluxed for 7 hours, cooled, stirred overnight about 16 hours at room temperature, filtered, and the solvent was evaporated to give an oil. The oil was purified on a silica gel column (250 g), eluting with 2% methanol/CHCl₃ to give 4.4 g of a solid. The solid was recrystallized twice from hexane to give 2.3 g (33%) of 1-methyl-4-(3-chlorobenzamido)-1-azaspiro[4.5]decane, m.p. 121°–122.5° C.

ANALYSIS: Calculated for $C_{17}H_{23}ClN_2O$: 66.54%C; 7.56%H; 9.13%N. Found: 66.35% C; 7.34%H; 8.99%N.

EXAMPLE 6

1-Methyl-4-(4-fluorobenzamido)-1-azaspiro[4.5]decane fumarate

To a stirring suspension of 3.5 g (0.021 mole) of 1-methyl-4-amino-1-azaspiro[4.5]decane of Example 2 in 150 ml of 10% NaOH solution was added dropwise 3.5 g (0.022 mole) of p-fluorobenzoyl chloride. The reaction was stirred for 18 hours at room temperature, the solid was collected by filtration and recrystallized from hexane to give 3.1 g of a solid. The resulting amide (0.01 mole) was dissolved in approximately 15 ml of acetonitrile and 1.24 g (0.011 mole) of fumaric acid was added. The mixture was stirred for 3 hours and the resulting precipitate was collected and recrystallized twice from ethanol-ether to give 2.1 g mole (25% yield) of 1-methyl-4-(4-fluorobenzamido)-1-azaspiro[4.5]decane fumarate, m.p. 187°–189° C.

ANALYSIS: Calculated for $C_{17}H_{24}N_2O \cdot C_4H_4O_4$: 62.05% C; 6.70%H; 6.89%N. Found: 61.89%C; 6.71%H; 6.87%N.

EXAMPLE 7

1-Methyl-4-benzamido-1-azaspiro[4.5]decane fumarate

To a stirring suspension of 3.5 g (0.021 mole) of 1-methyl-4-amino-1-azaspiro[4.5]decane of Example 2 and 150 ml of 10% NaOH was added dropwise 3.1 g (0.022 mole) of benzoyl chloride. The reaction was stirred vigorously for 24 hours, the aqueous solution was decanted and the remaining oil was dissolved in ethyl acetate and dried over $Na_2SO_4$. The solvent was then evaporated to give a solid which was recrystallized from hexane to give 2.5 g. The solid was dissolved in 10 ml of acetonitrile and 1.1 g of fumaric acid was added. The suspension was stirred until the amine salt precipitated from solution. The compound was filtered and recrystallized twice from ethanol-ether to give 2.1 g (25.7%) of 1-methyl-4-benzamido-1-azaspiro[4.5]decane fumarate, m.p. 171°–173° C.

ANALYSIS: Calculated for $C_{17}H_{24}N_2O \cdot C_4H_4O_4$: 64.93%C; 7.27%H; 7.21%N. Found: 64.89%C; 7.32%H; 7.18%N.

EXAMPLE 8

1-Methyl-4-(4-methylbenzamido)-1-azaspiro[4.5]decane fumarate

To a stirring suspension of 3.5 g (0.021 mole) of 1-methyl-4-amino-1-azaspiro[4.5]decane of Example 2 and 150 ml of 10% NaOH was added dropwise 3.5 g (0.022 mole) of p-toluoyl chloride. The reaction was stirred vigorously for 6 hours, the aqueous solution was decanted and the remaining oil was dissolved in ethyl acetate and dried over $Na_2SO_4$. The solvent was then evaporated to give 4.2 g of a solid which was recrystallized from hexane to give 3.2 g. The solid was dissolved in 20 ml of acetonitrile and 1.3 g of fumaric acid was added. The suspension was stirred until the amine salt precipitated from solution. The compound was filtered and recrystallized twice from ethanol-ether to give 3.0 g (35%) of 1-methyl-4-(4-methylbenzamido)-1-azaspiro[4.5]decane fumarate, m.p. 186°–188° C.

ANALYSIS: Calculated for $C_{18}H_{26}N_2O \cdot C_4H_4O_4$: 65.65%C; 7.51%H; 6.96%N. Found: 65.70%C; 7.52%H; 6.82%N.

EXAMPLE 9

1-Methyl-4-(4-methoxybenzamido)-1-azaspiro[4.5]decane hemifumarate

To a stirring suspension of 3.5 g (0.021 mole) of 1-methyl-4-amino-1-azaspiro[4.5]decane of Example 2 and 150 ml of 10% NaOH was added dropwise 3.8 g (0.022 mole) of p-anisoyl chloride. The reaction was stirred vigorously for 5 hours, the aqueous solution was decanted and the remaining oil was dissolved in ethyl acetate and dried over $Na_2SO_4$. The solvent was then evaporated to give a solid which was recrystallized from hexane to give 4.4 g. The solid was dissolved in 20 ml of acetonitrile and 1.7 g of fumaric acid was added. The suspension was stirred until the amine salt precipitated from solution. The compound was filtered and recrystallized twice from ethanol-ether to give 1.2 g (15.8%) of 1-methyl-4-(4-methoxybenzamido)-1-azaspiro[4.5]decane hemifumarate, m.p. (softens at 110° C.) 152°–155° C.

ANALYSIS: Calculated for $C_{18}H_{26}N_2O_2 \cdot \frac{1}{2}C_4H_4O_4$: 66.64%C; 7.83%H; 7.77%N. Found: 66.41%C; 7.61%H; 7.40%N.

EXAMPLE 10

1-Ethoxycarbonyl-4-(ethoxycarbonylamino)-1-azaspiro[4.5]decane

To a stirring suspension of 5.7 g of 1-ethoxycarbonyl-4-amino-1-azaspiro[4.5]decane of Example 1e and 7. g of $NaHCO_3$ in 100 ml of $CHCl_3$ was added in a dropwise fashion 3.8 g of ethyl chloroformate. The mixture was refluxed for 4 hours, cooled to room temperature, filtered, washed with water, 3 N-HCl, saturated sodium bicarbonate solution and saturated NaCl solution, dried over $Na_2SO_4$ and then evaporated to give 6 g of 1-ethoxycarbonyl-4-(ethoxycarbonylamino)-1-azaspiro[4.5]decane.

EXAMPLE 11

1-methyl-4-methylamino-1-azaspiro[4.5]decane

To a stirring solution of 2.4 g of lithium aluminum hydride (LAH) in 200 ml of THF was added in a dropwise manner 6.5 g of 1-ethoxycarbonyl-4-(ethoxycarbonylamino)-1-azaspiro[4.5]decane of Example 10 in 70 ml of THF. The resultant mixture was refluxed overnight, and then kept at room temperature for 48 hours. The excess LAH was destroyed with water, and the resultant mixture was filtered, washed with ether and then evaporated and then distilled at 55° C., 0.1 mm to yield 2.2 g of 1-methyl-4-methylamino-1-azaspiro[4.5]decane.

EXAMPLE 12

1-Methyl-4-(N-methyl-3,4-dichlorobenzamido)-1-azaspirio[4.5]decane

To a stirring suspension of 2.2 g (0.012 mole) of 1-methyl-4-methylamino-1-azaspiro[4.5]decane of Example 11 in 120 ml of 10% NaOH solution was added dropwise 2.6 g (0.013 mole) of 3,4-dichlorobenzoyl chloride. The reaction was stirred vigorously for 2 hours then filtered to give 3.7 g of a solid. The solid was recrystallized twice from $CH_3CN$ to give 1.3 g (30.5%) of 1-methyl-4-(N-methyl-3,4-dichlorobenzamido)-1-azaspiro[4.5]decane, m.p. 138.5°–140.5° C.

ANALYSIS: Calculated for $C_{18}H_{24}Cl_2N_2O$: 60.84%C; 6.81%H; 7.89%N; 19.96%Cl. Found: 61.03%C; 6.84%H; 7.88%N; 19.33%Cl.

EXAMPLE 13

1-Ethoxycarbonyl-4-methylamino-1-azaspiro[4.5]decane hydrochloride

Into a solution of 8.0 g (0.035 mole) of 1-ethoxycarbonyl-1-azaspiro[4.5]decane-4-one of Example 1d in 120 ml of anhydrous benzene and 180 ml of anhydrous ether cooled to −20° C. was bubbled an excess of 3.3 g (0.17 mole) of methylamine, then with stirring 2 ml (0.018 mole) of $TiCl_4$ in 20 ml of benzene was added dropwise. When the addition was complete the reaction was refluxed under nitrogen for 3 hours, cooled, filtered, and the solvent removed to give 10.6 g of the imine as an oil. The imine (10.6 g, 0.035 mole) was dissolved in 100 ml of absolute ethanol and added dropwise to a solution of 1.8 g (0.048 mole) of $NaBH_4$ in 100 ml of absolute ethanol. The reaction was refluxed under nitrogen for 18 hours, cooled to room temperature, poured into 600 ml of ice-3 N HCl, extracted with $CHCl_3$, basified with 6 N NaOH, extracted with $CHCl_3$, washed with saturated NaCl solution, dried over $Na_2SO_4$, and the excess solvent was removed to give 7.2 g (74%) of the carbamate as an oil. The hydrochloride salt was made by dissolving 3.0 g of the carbamate in ether and bubbling in HCl gas. The solid was collected, dried, and recrystallized twice from ethanol-ether to yield 1-ethoxycarbonyl-4-methylamino-1-azaspiro[4.5]decane hydrochloride, m.p. 207°–209° C.

ANALYSIS: Calculated for $C_{13}H_{24}N_2O_2 \cdot HCl$: 56.41%C; 9.10%H; 10.12%N. Found: 56.66%C; 9.17%H; 10.25%N.

EXAMPLE 14

1-Ethoxycarbonyl-4-N-methylbenzamido-1-azaspiro[4.5]decane

To a stirring suspension of 2.7 g (0.01 mole) of 1-ethoxycarbonyl-4-methylamino-1-azaspiro[4.5]decane of Example 13 and 4.6 g (0.05 mole) of $NaHCO_3$ in 30 ml of $CHCl_3$ was added 1.6 g (0.011 mole) of benzoyl chloride in 15 ml of $CHCl_3$. The reaction was refluxed for 18 hours, cooled, filtered, washed with water, 3 N HCl solution, saturated $NaHCO_3$ solution, saturated NaCl solution and was dried over $Na_2SO_4$. The solvent was removed under reduced pressure and the residue crystallized with scratching in hexane. The solid was recrystallized once from hexane to give 2.5 g (73%) of 1-ethoxycarbonyl-4-N-methylbenzamido-1-azaspiro[4.5]decane, m.p. 111°–112° C.

ANALYSIS: Calculated for $C_{20}H_{28}N_2O_3$: 69.74%C; 8.19%H; 8.13%N. Found: 69.75%C; 8.04%H; 8.01%N.

EXAMPLE 15

1-Ethoxycarbonyl-4-[N-methyl-3,4-dichlorobenzamido]-1-azaspiro[4.5]decane

To a stirring suspension of 2.0 g (0.007 mole) of 1-ethoxycarbonyl-4-methylamino-1-azaspiro[4.5]decane of Example 13 and 3.3 g of $NaHCO_3$ in 30 ml of $CHCl_3$ was added dropwise 1.6 g (0.008 mole) of 3,4-dichlorobenzoyl chloride in 15 ml of $CHCl_3$. The reaction was incomplete after 3 hours so an additional 10% of acid chloride was added and the reaction was refluxed for 18 hours, then cooled to room temperature, filtered, washed with $H_2O$, 3 N HCl solution, saturated $NaHCO_3$, saturated NaCl solution, and dried over $Na_2SO_4$. The solvent was removed under reduced pressure to give 4.1 g of an oil which was purified on a silica gel column (120 g) eluting with 1:1 ether/petroleum ether. The resulting solid was boiled in water, then taken up in $CHCl_3$. The $CHCl_3$ was evaporated to give a solid which was recrystallized once from hexane to give 1.8 g (62%) of 1-ethoxycarbonyl-4-[N-methyl-3,4-dichlorobenzamido]-1-azaspiro[4.5]decane, m.p. 57°–60° C.

ANALYSIS: Calculated for $C_{20}H_{26}Cl_2N_2O_3$: 58.11%C; 6.34%H; 6.82%N; 17.16%Cl. Found: 57.95%C; 6.33%H; 6.66%N; 16.89%Cl.

EXAMPLE 16

1-Ethoxycarbonyl-4-benzamido-1-azaspiro[4.5]decane

To a stirring suspension of 2.5 g (0.011 mole) of 1-ethoxycarbonyl-4-amino-1-azaspiro[4.5]decane of Example 1e and 4.5 g (0.05 mole) of $NaHCO_3$ in 30 ml of $CHCl_3$ was added 2.5 g (0.012 mole) of benzonyl chloride in 15 ml of $CHCl_3$. The reaction was refluxed for 2 hours, cooled to room temperature, filtered, washed with $H_2O$, 3 N HCl solution, saturated $NaHCO_3$ solution, saturated NaCl solution and dried over $Na_2SO_4$. The solvent was removed under reduced pressure to give 4.1 g of oil which was triturated with boiling $H_2O$. The water was decanted and the resulting solid was recrystallized twice from hexane to give 1.6 g (45%) of 1-ethoxycarbonyl-4-benzamido-1-azaspiro[4.5]decane, m.p. 132°–133° C.

ANALYSIS: Calculated for $C_{19}H_{26}N_2O_3$: 69.06%C; 7.93%H; 8.48%N. Found: 68.82%C; 7.97%H; 8.45%N.

EXAMPLE 17

1-Ethoxycarbonyl-4-[3,4-dichlorobenzamido]-1-azaspiro[4.5]decane

To a stirring suspension of 3.0 g (0.013 mole) of 1-ethoxycarbonyl-4-amino-1-azaspiro[4.5]decane of Example 1e and 4.5 g (0.05 mole) of $NaHCO_3$ in 40 ml of $CHCl_3$ was added dropwise 3.0 g (0.014 mole) of 3,4-dichloro benzoyl chloride in 20 ml of $CHCl_3$. The reaction was refluxed for 3 hours then cooled to room temperature, filtered, washed with $H_2O$, 3 N HCl solution, saturated NaCl solution, and dried over $Na_2SO_4$. The solvent was removed under reduced pressure to give an oil which was boiled in hexane to give 3.1 g of a solid. The solid was recrystallized from hexane to give 2.2 g (40%) of 1-ethoxycarbonyl-4-[3,4-dichlorobenzamido]-1-azaspiro[4.5]decane, m.p. 153°–155° C.

ANALYSIS: Calculated for $C_{19}H_{24}Cl_2N_2O_3$: 57.14%C; 6.06%H; 7.02%N; 17.76%Cl. Found: 57.31%C; 6.12%H; 7.00%N; 17.59%Cl.

EXAMPLE 18

1-Ethoxycarbonyl-4-[2,4-dichlorobenzamido]-1-azaspiro[4.5]decane

To a stirring suspension of 3.0 g of (0.013 mole) of 1-ethoxycarbonyl-4-amino-1-azaspiro[4.5]decane of Example 1e and 4.5 g (0.05 mole) of $NaHCO_3$ in 40 ml of $CHCl_3$ was added dropwise 3.0 g (0.014 mole) of 2,4-dichlorobenzoyl chloride in 20 ml of $CHCl_3$. The reaction was refluxed for 3 hours then cooled to room temperature, filtered, washed with $H_2O$, 3 N HCl solution, saturated $NaHCO_3$ solution, saturated NaCl solution and dried over $Na_2SO_4$. The solvent was removed under reduced pressure to give an oil which was boiled in hexane to give 3.4 g of a solid. The solid was recrystallized once from hexane to give 2.5 g (47%) of 1-ethoxycarbonyl-4-[2,4-dichlorobenzamido]-1-azaspiro[4.5]decane m.p. 143°–144° C.

ANALYSIS: Calculated for $C_{19}H_{24}Cl_2N_2O_3$: 57.14%C; 6.06%H; 7.02%N; 17.76%Cl. Found: 57.32%C; 6.11%H; 6.98%N; 17.70%Cl.

EXAMPLE 19 a. Ethyl-1-(3-Carboxycarbonylpropylamino)cyclohexanecarboxylate

A mixture of ethyl 4-bromobutyrate (34.1 g, 0.175 mole) $K_2CO_3$ (powdered, anhydrous, 24.2 g, 0.175 mole) and ethyl 1-aminocyclohexane carboxylate (30.0 g, 0.175 mole) was heated at 105° C. for 3 days. The mixture was poured into $H_2O$ and extracted thrice with $CH_2Cl_2$ (100 ml). The $CH_2Cl_2$ layers were combined, washed with $H_2O$, brine and $H_2O$, dried ($K_2CO_3$) and the solvent removed under reduced pressure to give a liquid, 41.0 g. This material was fractionally distilled at reduced pressure to yield, at 133°–135° C. and 0.50 mm Hg, 24.5 g of ethyl-1-(3-carboxycarbonylpropylamino)-cyclohexanecarboxylate.

b. Ethyl 1-(N-ethoxycarbonyl-N-3-ethoxycarbonylpropylamino)cyclohexanecarboxylate To a stirring mixture of ethyl 1-(3-carboethoxypropylamino)cyclohexanecarboxylate of Example 19a (24.5 g, 0.086 mole), $NaHCO_3$ (8.2 g, 0.098 mole) and $CHCl_3$ (150 ml) was added, dropwise, ethyl chloroformate (10.6 g, 0.098 mole) and the reaction allowed to stir and reflux for 16 hours. The mixture was poured into $H_2O$, and the $CHCl_3$ layer separated. The $CHCl_3$ layer was washed with dilute HCl, $H_2O$, dried ($K_2CO_3$) and the solvent removed under reduced pressure to give 31.2 g of clear liquid. Fractional distillation under reduced pressure gave 23.5 g (76.5%) of a liquid of ethyl 1-(N-ethoxycarbonyl-N-3-ethoxycarbonylpropylamino)cyclohexanecarboxylate which distilled at 146° C. and 0.15 mm.

ANALYSIS: Calculated for $C_{18}H_{31}NO_6$: 60.48%C; 8.74%H; 3.92%N. Found: 60.59%C; 8.85%H; 3.81%N.

c. 1-Ethoxycarbonyl-1-azaspiro[5.5]undecan-5-one

To a stirring suspension under nitrogen of NaH (5.6 g 0.13 mole, of a 50% oil dispersion) in benzene (50 ml.) was added dropwise ethyl-1-(N-ethoxycarbonyl-N-3-ethoxycarbonylpropylamino)cyclohexanecarboxylate (22.0 g 0.062 mole) in benzene (30 ml). The reaction was stirred and refluxed for 3 hours. After cooling the mixture was poured into ice-3 N HCl, the layers were separated and the aqueous phase was extracted with benzene twice. The benzene layers were combined, washed with water, brine and water, then the benzene layer was dried ($Na_2SO_4$) and the solvent removed under vacuum. The resultant oil weighed 19.2 g. The oil was then refluxed with 6 N HCl for 2 hours, cooled and the acidic solution extracted with benzene twice. The benzene extracts were combined, dried ($Na_2SO_4$) and the solvent removed under reduced pressure to yield a liquid. The liquid was then refluxed with ethanol (50 ml) 6 N HCl (100 ml) for 2 hours. After cooling to room temperature, most of the ethanol was removed under reduced pressure and the resultant aqueous suspension was extracted twice with ether (75 ml). The ether extracts were combined, washed with $H_2O$, saturated $Na_2HCO_3$, then $H_2O$, dried ($K_2CO_3$) and the ether evaporated to give 10.5 g of a liquid. This material was fractionally distilled under vacuum to yield, at 160° C. and 0.15 mm Hg pressure, 8.4 g (57%) of 1-ethoxycarbonyl-1-azaspiro[5.5]undecan-5-one.

d. 5-Amino-1-ethoxycarbonyl-1-azaspiro[5.5]undecane hydrochloride

A mixture of the azaspiro ketone of Example 19c, (1.0, 0.004 mole), $NaBH_3CN$ (0.17 g, 0.0028 mole) ammonium acetate (3.1 g, 0.04 mole) and several 3A molecular sieves in absolute methanol (20 ml), was stirred and refluxed under nitrogen for 21 hours. The reaction was permitted to cool, then it was acidified to pH 2 with concentrated HCl. The methanol was removed in vacuo and the resultant residue was dissolved in $H_2O$ and the solution extracted with ether. The aqueous solution was basified with 50% aqueous NaOH, then extracted twice with ether (100 ml). The ether extracts were combined, washed with $H_2O$, dried ($K_2CO_3$) and the ether evaporated to give 0.6 g of an oil. The oil was dissolved in ether and HCl(g) bubbled in to precipitate a white hydrochloride salt 0.5 g (45%), m.p. 269°–270° (dec.). Recrystallization from ethanol-ether gave 0.33 g of 5-amino-1-ethoxycarbonyl-1-azaspiro[5.5]undecane hydrochloride.

ANALYSIS: Calculated for $C_{13}H_{24}N_2O_2 \cdot HCl$: 56.41%C; 9.10%H; 10.12%N. Found: 56.26%C; 9.02%H; 10.02%N.

e. 1-Ethoxycarbonyl-5-(3,4-dichlorobenzamido)-1-azaspiro[5.5]undecane

A suspension of 4.9 g (0.020 mole) of 5-amino-1-ethoxycarbonyl-1-azaspiro[5.5]undecane and 4.6 g (0.022 mole) of 3,4-dichlorobenzoyl chloride was stirred vigorously in 200 ml of 10% NaOH solution for 2 hours. The aqueous solution was decanted and the gummy solid was dissolved in ethyl acetate and dried over $Na_2SO_4$. The ethyl acetate was removed under reduced pressure and the residue was triturated with boiling hexane. Filtration yielded 4.8 g of a solid which was recrystallized twice from hexane to give 3.6 g (43.5%) of 1-ethoxycarbonyl-5-(3,4-dichlorobenzamido)-1-azaspiro[5.5]undecane, m.p. 74°–77° C.

ANALYSIS: Calculated for $C_{20}H_{26}Cl_2N_2O_3$: 58.11%C; 6.34%H; 6.78%N. Found: 58.41%C; 6.30%H; 6.54%N.

EXAMPLE 20

1-Azaspiro[4.5]decane-4-one hydrochloride

To a solution of 45 ml of acetic acid and 5 ml of $H_2O$ saturated with HBr was added 3.0 g (0.013 mole) of 1-ethoxycarbonyl-1-azaspiro[4.5]decane-4-one of Example 1d. The reaction was refluxed for 4 hours then poured into 100 ml of $H_2O$ and extracted once with ether. The aqueous solution was basified with 25% NaOH solution and extracted with ether twice. The ether extracts were washed with saturated NaCl solution and dried over $Na_2SO_4$. The solvent was removed to give 1.0 g of an oil which was dissolved in ether into which HCl gas was bubbled. The precipitate was recrystallized three times from ethanol-ether to give 0.65 g (30%) of 1-azaspiro[4.5]decane-4-one hydrochloride, m.p. 157°–158° C.

ANALYSIS: Calculated for $C_9H_{15}NO \cdot HCl$: 56.99%C; 8.50%H; 7.38%N; 18.69%Cl. Found: 56.78%C; 8.33%H; 7.36%N; 18.47%Cl.

It is predicted that the resultant 1-azaspiro[4.5]decane-4-one hydrochloride can be treated in a similar fashion to that described in Example 1e above to obtain 4-amino-1-azaspiro[4.5]decane.

EXAMPLE 21

1-β-phenethyl-1-azaspiro[4.5]decane-4-one hydrochloride

To a stirring suspension of 5.7 g (0.037 mole) of 1-azaspiro[4.5]decane-4-one of Example 20, 5.4 g (0.064 mole) of NaHCO$_3$, and 3.0 g (0.02 mole) of KI in 100 ml of dimethylformamide (DMF) was added dropwise 7.6 g (0.040 mole) of phenethyl bromide in 20 ml of DMF. The reaction was stirred at 55° C. for 30 hours, cooled to room temperature, filtered, poured into 500 ml of H$_2$O and extracted with ether (3 times). The ether extracts were washed with saturated NaCl solution, dried over Na$_2$SO$_4$ and the ether was removed under reduced pressure. The residue was dissolved in ether and a solution of ethanol-HCl was added. The solid was collected and recrystallized 3 times from ethanol-ether to give 4.6 g (42%) of 1-β-phenethyl-1-azaspiro[4.5]decane-4-one hydrochloride, m.p. 205°–207° C.

ANALYSIS: Calculated for C$_{17}$H$_{23}$NO.HCl: 69.49%C; 8.23%H; 4.76%N. Found: 69.33%C; 8.27%H; 4.78%N.

It is predicted that the resultant 1-phenethyl-1-azaspiro[4.5]decane-4-one hydrochloride can be treated in a similar fashion to that described in Example 1e above to obtain 1-β-phenethyl-4-amino-1-azaspiro[4.5]decane.

We claim:

1. A compound having the formula

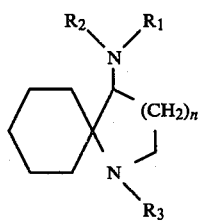

wherein R$_1$ is hydrogen, CO$_2$R$_4$, R$_4$; R$_2$ is hydrogen,

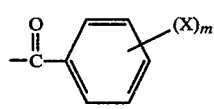

R$_3$ is hydrogen, —CO$_2$ R$_5$, R$_5$,

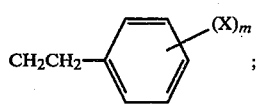

R$_4$ is alkyl of 1 to 4 carbon atoms; R$_5$ is alkyl of 1 to 8 carbon atoms; X is halogen, alkyl of 1 to 4 carbon atoms, alkoxy of 1 to 4 carbon atoms, CF$_3$, and OH; m is an integer of 0, 1 or 2, and n is an integer of 1 or 2 or its pharmaceutically acceptable salts thereof.

2. A compound as defined in claim 1 wherein R$_1$ is —CO$_2$R$_4$—

3. The compound as defined in claim 2 wherein R$_3$ is R$_5$.

4. The compound as defined in claim 1 wherein R$_3$ is

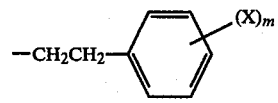

5. The compound as defined in claim 4 wherein X is OH.

6. The compound as defined in claim 4 wherein X is CF$_3$.

7. The compound as defined in claim 1 which is 1-ethoxycarbonyl-4-amino-1-azaspiro[4.5]decane or a pharmaceutically acceptable salt thereof.

8. The compound as defined in claim 1 which is 1-methyl-4-amino-1-azaspiro[4.5]decane or a pharmaceutically acceptable salt thereof.

9. The compound as defined in claim 1 which is 1-methyl-4-(3,4-dichlorobenzamido)-1-azaspiro[4.5]decane or a pharmaceutically acceptable salt thereof.

10. The compound as defined in claim 1 which is 1-methyl-4-(2,4-dichlorobenzamido)-1-azaspiro[4.5]decane or a pharmaceutically acceptable salt thereof.

11. The compound as defined in claim 1 which is 1-methyl-4-(3-chlorobenzamido)-1-azaspiro[4.5]decane or a pharmaceutically acceptable salt thereof.

12. The compound as defined in claim 1 which is 1-methyl-4-(4-fluorobenzamido)-1-azaspiro[4.5]decane or a pharmaceutically acceptable salt thereof.

13. The compound as defined in claim 1 which is 1-methyl-4-benzamido-1-azaspiro[4.5]decane or a pharmaceutically acceptable salt thereof.

14. The compound as defined in claim 1 which is 1-methyl-4-(4-methylbenzamido)-1-azaspiro[4.5]decane or a pharmaceutically acceptable salt thereof.

15. The compound as defined in claim 1 which is 1-methyl-4-(4-methoxybenzamido)-1-azaspiro[4.5]decane or a pharmaceutically acceptable salt thereof.

16. The compound as defined in claim 1 which is 1-ethoxy-4-(ethoxycarbonylamino)-1-azaspiro[4.5]decane or a pharmaceutically acceptable salt thereof.

17. The compound as defined in claim 1 which is 1-methyl-4-methylamino-1-azaspiro[4.5]decane or a pharmaceutically acceptable salt thereof.

18. The compound as defined in claim 1 which is 1-methyl-4-(N-methyl-3,4-dichlorobenzamido)-1-azaspiro[4.5]decane or a pharmaceutically acceptable salt thereof.

19. The compound as defined in claim 1 which is 1-ethoxycarbonyl-4-methylamino-1-azaspiro[4.5]decane or a pharmaceutically acceptable salt thereof.

20. The compound as defined in claim 1 which is 1-ethoxycarbonyl-4-(N-methylbenzamido)-1-azaspiro[4.5]decane or a pharmaceutically acceptable salt thereof.

21. The compound as defined in claim 1 which is 1-ethoxycarbonyl-4-[N-methyl-3,4-dichlorobenzamido]-1-azaspiro[4.5]decane or a pharmaceutically acceptable salt thereof.

22. The compound as defined in claim 1 which is 1-ethoxycarbonyl-4-benzamido-1-azaspiro[4.5]decane or a pharmaceutically acceptable salt thereof.

23. The compound as defined in claim 1 which is 1-ethoxycarbonyl-4-[3,4-dichlorobenzamido]-1-azaspiro[4.5]decane or a pharmaceutically acceptable salt thereof.

24. The compound as defined in claim 1 which is 1-ethoxycarbonyl-4-[2,4-dichlorobenzamido]-1-azaspiro[4.5]decane or a pharmaceutically acceptable salt thereof.

25. The compound as defined in claim 1 which is 1-ethoxycarbonyl-5-(3,4-dichlorobenzamido)-1-azaspiro[5.5]undecane or a pharmaceutically acceptable salt thereof.

26. An analgesic composition which comprises an amount effective in reducing pain of a compound of claim 1 together with a suitable pharmaceutically acceptable carrier.

27. The analgesic composition of claim 26 wherein $R_1$ of the compound is $-CO_2R_4$.

28. The analgesic composition of claim 26 wherein $R_3$ of the compound is $R_5$.

29. The analgesic composition of claim 26 wherein $R_3$ of the compound is

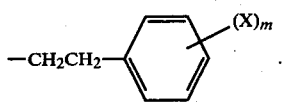

30. The analgesic composition of claim 26 wherein X of the compound is OH.

31. The analgesic composition of claim 26 wherein X of the compound is $CF_3$.

32. The analgesic composition of claim 26 which comprises 1-ethoxycarbonyl-4-amino-1-azaspiro[4.5]decane or a pharmaceutically acceptable salt thereof.

33. The analgesic composition of claim 26 which comprises 1-methyl-4-amino-1-azaspiro[4.5]decane or a pharmaceutically acceptable salt thereof.

34. The analgesic composition of claim 26 which comprises 1-methyl-4-(3,4-dichlorobenzamido)-1-azaspiro[4.5]decane or a pharmaceutically acceptable salt thereof.

35. The analgesic composition of claim 26 which comprises 1-methyl-4-(2,4-dichlorobenzamido)-1-azaspiro[4.5]decane or a pharmaceutically acceptable salt thereof.

36. The analgesic composition of claim 26 which comprises 1-methyl-4-(3-chlorobenzamido)-1-azaspiro[4.5]decane or a pharmaceutically acceptable salt thereof.

37. The analgesic composition of claim 26 which comprises 1-methyl-4-(4-fluorobenzamido)-1-azaspiro[4.5]decane or a pharmaceutically acceptable salt thereof.

38. The analgesic composition of claim 26 which comprises 1-methyl-4-benzamido-1-azaspiro[4.5]decane or a pharmaceutically acceptable salt thereof.

39. The analgesic composition of claim 26 which comprises 1-methyl-4-(4-methylbenzamido)-1-azaspiro[4.5]decane or a pharmaceutically acceptable salt thereof.

40. The analgesic composition of claim 26 which comprises 1-methyl-4-(4-methoxybenzamido)-1-azaspiro[4.5]decane or a pharmaceutically acceptable salt thereof.

41. The analgesic composition of claim 26 which comprises 1-ethoxy-4-(ethoxycarbonylamino)-1-azaspiro[4.5]decane or a pharmaceutically acceptable salt thereof.

42. The analgesic composition of claim 26 which comprises 1-methyl-4-methylamino-1-azaspiro[4.5]decane or a pharmaceutically acceptable salt thereof.

43. The analgesic composition of claim 26 which comprises 1-methyl-4-(N-methyl-3,4-dichlorobenzamido)-1-azaspiro[4.5]decane or a pharmaceutically acceptable salt thereof.

44. The analgesic composition of claim 26 which comprises 1-ethoxycarbonyl-4-methylamino-1-azaspiro[4,5]decane or a pharmaceutically aceptable salt thereof.

45. The analgesic composition of claim 26 which comprises 1-ethoxycarbonyl-4-(n-methylbenzamido)-1-azaspiro[4.5]decane or a pharmaceutically acceptable salt thereof.

46. The analgesic composition of claim 26 which comprises 1-ethoxycarbonyl-4-[N-methyl-3,4-dichlorobenzamido]-1-azaspiro[4.5]decane or a pharmaceutically acceptable salt thereof.

47. The analgesic composition of claim 26 which comprises 1-ethoxycarbonyl-4-benzamido-1-azaspiro[4.5]decane or a pharmaceutically acceptable salt thereof.

48. The analgesic composition of claim 26 which comprises 1-ethoxycarbonyl-4-[3,4-dichlorobenzamido]-1-azaspiro[4.5]decane or a pharmaceutically acceptable salt thereof.

49. The analgesic composition of claim 26 which comprises 1-ethoxycarbonyl-4-[2,4-dichlorobenzamido]-1-azaspiro[4.5]decane or a pharmaceutically acceptable salt thereof.

50. The analgesic composition of claim 26 which comprises 1-ethoxycarbonyl-5-(3,4-dichlorobenzamido)-1-azaspiro[5.5]undecane or a pharmaceutically acceptable salt thereof.

51. A method of preparing a compound of the formula

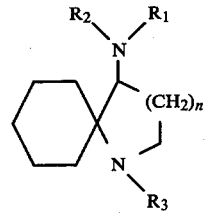

wherein $R_1$ is hydrogen,

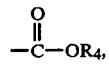

$R_4$; $R_2$ is hydrogen,

$R_3$ is hydrogen,

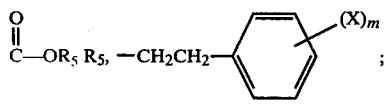

$R_4$ is alkyl of 1 to 4 carbon atoms; $R_5$ is alkyl of 1 to 8 carbon atoms; x is halogen; alkyl of 1 to 4 carbon atoms, alkoxy of 1 to 4 carbon atoms, $CF_3$ and OH; m is an integer of 0, 1 or 2 and n is an integer of 1 or 2 or its pharmaceutically acceptable salts thereof, which comprises reacting a compound having the formula

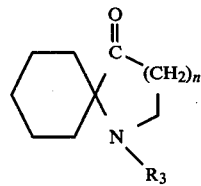

with sodium cyanoborohydride to form a reaction product having the formula

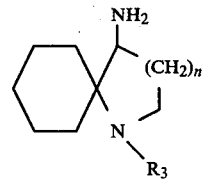

52. The method as defined in claim 51 which further comprises reacting said reaction product with a reactant selected from (1) Hal $R_1$, where Hal is a halogen and $R_1$ is as previously defined and is other than hydrogen, (2) Hal $R_2$, where Hal is a halogen and $R_2$ is as previously defined and is other than hydrogen and (3) reactants (1) and (2).

* * * * *

UNITED STATES PATENT AND TRADEMARK OFFICE
CERTIFICATE OF CORRECTION

PATENT NO. : 4,430,335

DATED : February 7, 1984

INVENTOR(S) : Joseph T. Strupczewski
Beth A. Gardner

It is certified that error appears in the above-identified patent and that said Letters Patent is hereby corrected as shown below:

Column 1, line 52, change "$R_1$" to --$R_2$--;

Column 9, line 11, after "(30° - 60°C.)" delete the comma (,);

Column 15, lines 10 and 22, change "carboxycarbonyl" to --carboethoxy--.

Signed and Sealed this

Seventh Day of May 1985

[SEAL]

Attest:

DONALD J. QUIGG

Attesting Officer

Acting Commissioner of Patents and Trademarks